United States Patent [19]

Holtkamp

[11] Plant 4,521

[45] Apr. 15, 1980

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "OPTIMARA", Isselburg, Fed. Rep. of Germany

[21] Appl. No.: 15,679

[22] Filed: Feb. 27, 1979

[51] Int. Cl.[2] ..... A01H 5/00

[52] U.S. Cl. ..... Plt./69

[58] Field of Search ..... Plt./69

*Primary Examiner*—Robert E. Bagwill
*Attorney, Agent, or Firm*—Donald D. Jeffery

[57] ABSTRACT

An African violet plant known by the cultivar name San Francisco having girl type leaves, star-shaped lilac colored flowers carried on strong and upright stems, vigorous growth habit, compact bouquet and habit, and by its non-dropping, long lasting flowers.

1 Drawing Figure

The present invention comprises a new and distinct cultivar of African violet plant, botanically known as *Saintpaulia ionantha,* and hereinafter referred to by the cultivar name San Francisco.

The new cultivar was referred to during the breeding and selection process by the designation B 234/10-91/79, and is a product of a planned breeding program.

San Francisco is generally characterized by its attractive medium green leaves with bright green centers, referred to in the industry as "girl" type leaves. Even without flowers, the leaves provide a very attractive plant. Star-shaped, lilac colored flowers are carried on strong and upright stems, providing an attractive bouquet above the leaves. San Francisco is a vigorous grower. These traits in combination were not present in previously available commercial cultivars.

The new cultivar was originated from a cross made in a controlled breeding program in Isselburg, Rhineland, Germany. The female, or seed parent was a cultivar designated XX 89 Girl light blue star, an unpatented cultivar. The male, or pollen parent was a cultivar designated LS blue single, also unpatented.

The new cultivar San Francisco was discovered and selected as a flowering plant within the progeny of the stated cross by be in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of San Francisco, which in combination distinguish this African violet as a new and distinct cultivar:

(1) Attractive colorful leaves having light green centers, shiny and wavy-like surfaces, serrated edges, and slightly hairy.

(2) Strong upright flower stems, 7 and more on a mature plant, with 5-7 flowers per stem.

(3) Star-shaped flowers, lilac in color, with the petals being normally five in number and equal in size, with a few flowers having an additional small petal in the center attached to the filament.

(4) Vigorous growth habit.

(5) Compact bouquet and habit.

The accompanying photographic drawing shows a typical specimen plant of the new cultivar. The colors appearing in the photograph are as true as possible with color illustrations of this type.

In the following description, color references are made both to the Royal Horticultural Society color chart (RHS) and the Horticultural Color Chart (HCC) issued by Wilson Colour Ltd. in order to provide the most accurate color values.

Botanical classification: *Saintpaulia ionantha,* Ramat. cv San Francisco.

Parentage:

*Male parent.*—SL blue single.

*Female parent.*—XX 89 Girl light blue star.

Propagation: The new cultivar holds its distinguishing characteristics through successive propagations by leaf cuttings and by division of shoots.

Plant: From 7 cm. to 10 cm. tall when grown in pots, and approximately 18-22 cm. in diameter when fully grown.

Leaves:

*General form.*—Generally round, one side funnel-shaped (girl type).

*Diameter.*—50-60 mm.

*Texture.*—Soft.

*Aspect.*—Borders are moderately to strongly serrated.

*Veins.*—On underside well pronounced.

*Color (upperside).*—RHS yellow green 147 A.

*Color (underside).*—HHC leek green 00858/2.

*Petiole.*—Short and strong, hairy, having a groove on the upperside.

Flowers:

*Buds.*—Bell shaped, 6-7 mm. before opening.

*Sepals.*—5 in number. Calyx: funnel-shaped, flat. Aspect: spear-shaped, hairy. Peduncle: short, strong, brownish, hairy.

Individual flowers:

*Size.*—40-50 mm., flat funnel.

*Color.*—Upperside: RHS purple-violet, between 82A-B. Underside: RHS purple-violet 82B.

*Borne.*—Profusely in a central flower head forming a compact bouquet above foliage.

*Shape.*—Star-shaped; 5 petals same size; a few flowers have additional small petal in the center joined with filament; also between the petals on some flowers is an additional small petal.

*Arrangement.*—4–7 single flowers appear on short peduncle.

*Flowering time.*—6 weeks after potting the first flowers appear; 8–10 weeks is needed to full maturity with a full flower head. The plant shown in the photograph is 7 weeks following potting.

Reproductive organs:

*Stamens.*—4–5 in number.

*Anthers.*—8–10 close together, color RHS yellow 18 A.

*Arrangement.*—The stamens have 4–5 short stems and are arranged around the seed bud; some petals are joined to the filament.

*Filament.*—Light green, oval, violet stripes, 5–6 mm. long.

*Styles.*—RHS violet 87 A.

*Pollen color.*—RHS yellow orange 18 C.

Roots: Normally developed, white when young, turning brownish when older.

Disease resistance: No disease noticed to date.

General observations: San Francisco is a vigorous grower with very compact habit. Due to the interesting form and color of the leaves, this variety is attractive without flowers. The strong and upright flower stems carry between 4 and 7 flowers per stem, with the flowers being star-shaped, lilac in color, non-dropping and very long lasting.

I claim:

1. A new and distinct cultivar of African violet plant as shown and described, known by the cultivar name San Francisco and characterized by the combined features of girl type leaves, star-shaped lilac colored flowers carried on strong and upright stems, vigorous growth habit, compact bouquet and habit, and by its non-dropping, long lasting flowers.

* * * * *

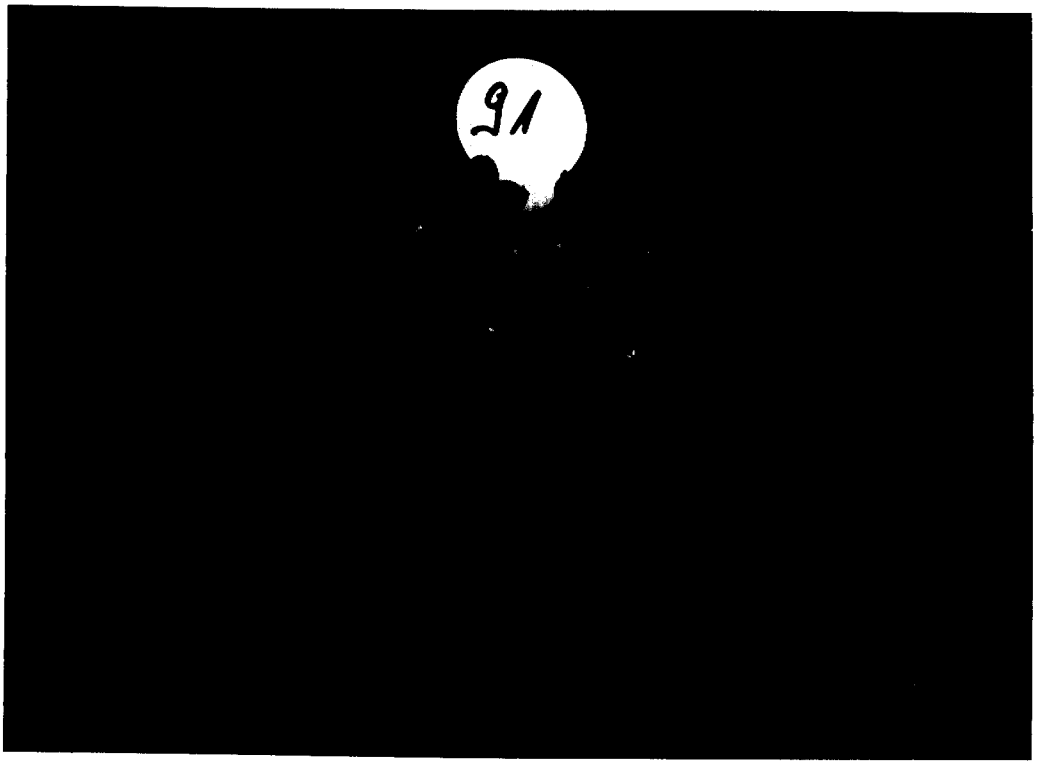
91